United States Patent
Markosyan

(10) Patent No.: US 11,279,773 B2
(45) Date of Patent: Mar. 22, 2022

(54) **PRODUCTS FROM *STEVIA RABAUDIANA***

(71) Applicant: PureCircle Sdn Bhd, Kuala Lumpur (MY)

(72) Inventor: Avetik Markosyan, Yerevan (AM)

(73) Assignee: PureCircle Sdn Bhd, Kuala Lumpur (MY)

( * ) Notice: Subject to any disclaimer, the term of this patent is extended or adjusted under 35 U.S.C. 154(b) by 0 days.

(21) Appl. No.: 16/747,421

(22) Filed: Jan. 20, 2020

(65) Prior Publication Data

US 2020/0148792 A1     May 14, 2020

Related U.S. Application Data

(60) Continuation of application No. 15/714,311, filed on Sep. 25, 2017, now abandoned, which is a division of application No. 14/829,127, filed on Aug. 18, 2015, now Pat. No. 9,771,434, which is a continuation-in-part of application No. 14/195,812, filed on Mar. 3, 2014, now abandoned, which is a continuation-in-part of application No. 13/943,776, filed on Jul. 16, 2013, now Pat. No. 10,368,570, which is a division of application No. 13/530,113, filed on Jun. 22, 2012, now Pat. No. 8,530,527.

(60) Provisional application No. 62/172,525, filed on Jun. 8, 2015, provisional application No. 61/500,598, filed on Jun. 23, 2011.

(51) Int. Cl.
  *C08B 15/02* (2006.01)
  *C12P 19/56* (2006.01)
  *A23L 27/30* (2016.01)
  *C13K 1/02* (2006.01)

(52) U.S. Cl.
  CPC ............. *C08B 15/02* (2013.01); *A23L 27/36* (2016.08); *C12P 19/56* (2013.01); *C13K 1/02* (2013.01)

(58) Field of Classification Search
  None
  See application file for complete search history.

(56) References Cited

U.S. PATENT DOCUMENTS

| | | | |
|---|---|---|---|
| 2,500,173 A | 3/1950 | Gisvold | |
| 2,615,015 A | 10/1952 | Wilson | |
| 3,723,410 A | 3/1973 | Beall et al. | |
| 4,082,858 A | 4/1978 | Morita et al. | |
| 4,112,218 A | 9/1978 | Inoue et al. | |
| 4,171,430 A | 10/1979 | Ikushige et al. | |
| 4,219,571 A | 8/1980 | Miyake | |
| 4,361,697 A | 11/1982 | Dobberstein et al. | |
| 4,454,290 A | 6/1984 | Dubois | |
| 4,590,160 A | 5/1986 | Nishihashi et al. | |
| 4,599,403 A | 7/1986 | Kumar | |
| 4,612,942 A | 9/1986 | Dobberstein et al. | |
| 4,657,638 A | 4/1987 | Le Grand et al. | |
| 4,892,938 A | 1/1990 | Giovanetto | |
| 4,915,969 A | 4/1990 | Beyts | |
| 4,917,916 A | 4/1990 | Hirao et al. | |
| 5,047,332 A | 9/1991 | Chahal | |
| 5,112,610 A | 5/1992 | Kienle | |
| 5,250,300 A | 10/1993 | Dozono | |
| 5,576,042 A | 11/1996 | Fuisz | |
| 5,779,805 A | 7/1998 | Morano | |
| 5,830,523 A | 11/1998 | Takaichi et al. | |
| 5,962,678 A | 10/1999 | Payzant et al. | |
| 5,972,120 A | 10/1999 | Kutowy et al. | |
| 6,031,157 A | 2/2000 | Morita et al. | |
| 6,080,561 A | 6/2000 | Morita et al. | |
| 6,204,377 B1 | 3/2001 | Nishimoto et al. | |
| 6,228,996 B1 | 5/2001 | Zhou et al. | |
| 6,318,157 B1 | 11/2001 | Corso et al. | |
| 6,706,304 B1 | 3/2004 | Ishida et al. | |
| 7,335,389 B2 | 2/2008 | Lerchenfeld et al. | |
| 7,579,032 B2 | 8/2009 | Lee et al. | |
| 7,807,206 B2 | 10/2010 | Magomet et al. | |
| 7,815,956 B2 | 10/2010 | Lee et al. | |
| 7,838,044 B2 | 11/2010 | Abelyan et al. | |
| 7,862,845 B2 | 1/2011 | Magomet et al. | |
| 7,923,541 B2 | 4/2011 | Yang et al. | |
| 7,923,552 B2 | 4/2011 | Jackson et al. | |
| 7,927,851 B2 | 4/2011 | Brandle et al. | |
| 7,964,232 B2 | 6/2011 | Lee | |
| 7,993,689 B2 | 8/2011 | Duan et al. | |
| 8,017,168 B2 | 9/2011 | Prakash et al. | |
| 8,030,481 B2 | 10/2011 | Prakash et al. | |
| 8,052,999 B2 | 11/2011 | Politi et al. | |
| 8,257,948 B1 | 9/2012 | Markosyan | |
| 8,277,862 B2 | 10/2012 | Lee et al. | |
| 8,298,599 B2 | 10/2012 | Abelyan et al. | |

(Continued)

FOREIGN PATENT DOCUMENTS

| | | |
|---|---|---|
| CN | 1049666 | 3/1991 |
| CN | 1100727 | 3/1995 |

(Continued)

OTHER PUBLICATIONS

Kinghorn (in "Medicinal and Aromatic Plants—Industrial Profiles", vol. 19: Stevia, 2002) (Year: 2002).*
Kamauchi et al (Tetrahedron Letters 55:7203-7205, 2014) (Year: 2014).*
Kamauchi et al (Tetrahedron Letters 56:4377-4382, 2015) (Year: 2015).*
Kochikyan, et al. "Combined Enzymatic Modification of Stevioside and Rebaudioside A", Applied Biochemistry and Microbiology, vol. 42, No. 1, 2006, 31-37.
Kohda, et al., "New sweet diterpene glucosides from Stevia Rebaudiana", Phytochemistry, vol. 15 1976, 981-983.
Kovylyaeva, et al., "Glycosides from Stevia rebaudiana", Chemistry of Natural Compounds, vol. 43, No. 1 2007, 81-85.

(Continued)

*Primary Examiner* — Craig D Ricci
(74) *Attorney, Agent, or Firm* — Rachael Casey

(57) ABSTRACT

Various organic molecules, ingredients and compositions are prepared from *Stevia rebaudiana* plant. The compositions can be used as bulking agents, and sweeteners in foods, beverages, cosmetics and pharmaceuticals.

5 Claims, No Drawings

(56) References Cited

U.S. PATENT DOCUMENTS

| | | | |
|---|---|---|---|
| 8,299,224 B2 | 10/2012 | Abelyan et al. |
| 8,318,232 B2 | 11/2012 | Abelyan et al. |
| 8,318,459 B2 | 11/2012 | Markosyan |
| 8,324,375 B2 | 12/2012 | Watanabe et al. |
| 8,334,006 B2 | 12/2012 | Purkayastha et al. |
| 8,337,927 B2 | 12/2012 | Purkayastha et al. |
| 8,367,137 B2 | 2/2013 | Prakash et al. |
| 8,367,138 B2 | 2/2013 | Prakash et al. |
| 8,377,491 B2 | 2/2013 | Prakash et al. |
| 8,435,587 B2 | 5/2013 | Prakash et al. |
| 8,435,588 B2 | 5/2013 | Prakash et al. |
| 8,512,789 B2 | 8/2013 | Prakash et al. |
| 8,524,303 B2 | 9/2013 | Prakash et al. |
| 8,524,304 B2 | 9/2013 | Prakash et al. |
| 8,530,527 B2 | 9/2013 | Markosyan |
| 8,646,458 B2 | 2/2014 | Bernard |
| 8,647,844 B2 | 2/2014 | Markosyan |
| 8,669,077 B2 | 3/2014 | Markosyan |
| 8,703,224 B2 | 4/2014 | Lee |
| 8,709,521 B2 | 4/2014 | Prakash et al. |
| 8,709,527 B2 | 4/2014 | Fouache et al. |
| 8,735,101 B2 | 5/2014 | Markosyan |
| 8,752,417 B2 | 6/2014 | Valery et al. |
| 8,764,822 B2 | 7/2014 | Harris et al. |
| 8,790,730 B2 | 7/2014 | Markosyan et al. |
| 8,791,253 B2 | 7/2014 | Prakash et al. |
| 8,911,971 B2 | 12/2014 | Markosyan |
| 8,937,168 B2 | 1/2015 | Evans et al. |
| 8,940,350 B2 | 1/2015 | Prakash et al. |
| 8,940,351 B2 | 1/2015 | Prakash et al. |
| 8,945,652 B2 | 2/2015 | Prakash et al. |
| 8,956,677 B2 | 2/2015 | Prakash et al. |
| 8,956,678 B2 | 2/2015 | Prakash et al. |
| 8,962,058 B2 | 2/2015 | Prakash et al. |
| 8,993,027 B2 | 3/2015 | Prakash |
| 8,993,269 B2 | 3/2015 | Markosyan |
| 9,011,956 B2 | 4/2015 | Prakash et al. |
| 9,012,520 B2 | 4/2015 | Prakash et al. |
| 9,012,626 B2 | 4/2015 | Prakash et al. |
| 9,055,761 B2 | 6/2015 | Markosyan |
| 9,101,160 B2 | 8/2015 | Prakash et al. |
| 9,101,161 B2 | 8/2015 | Prakash et al. |
| 9,115,166 B2 | 8/2015 | Prakash et al. |
| 9,131,718 B2 | 9/2015 | Shi et al. |
| 9,144,251 B2 | 9/2015 | Prakash et al. |
| 9,284,570 B2 | 3/2016 | Stephanopoulos et al. |
| 9,603,373 B2 | 3/2017 | Markosyan |
| 9,717,267 B2 | 8/2017 | Prakash et al. |
| 9,752,174 B2 | 9/2017 | Markosyan et al. |
| 9,790,351 B2 | 10/2017 | Szente |
| 9,877,500 B2 | 1/2018 | Lee et al. |
| 2002/0132320 A1 | 9/2002 | Wang et al. |
| 2002/0187232 A1 | 12/2002 | Lee et al. |
| 2003/0161876 A1 | 8/2003 | Hansson et al. |
| 2003/0236399 A1 | 12/2003 | Zheng et al. |
| 2006/0142555 A1 | 6/2006 | Jonnala et al. |
| 2007/0116800 A1 | 5/2007 | Prakash et al. |
| 2007/0116820 A1 | 5/2007 | Prakash et al. |
| 2007/0116822 A1 | 5/2007 | Prakash et al. |
| 2007/0116823 A1 | 5/2007 | Prakash et al. |
| 2007/0116825 A1 | 5/2007 | Prakash et al. |
| 2007/0116829 A1 | 5/2007 | Prakash et al. |
| 2007/0116831 A1 | 5/2007 | Prakash et al. |
| 2007/0116833 A1 | 5/2007 | Prakash et al. |
| 2007/0116836 A1 | 5/2007 | Prakash et al. |
| 2007/0116839 A1 | 5/2007 | Prakash et al. |
| 2007/0134391 A1 | 6/2007 | Prakash et al. |
| 2008/0102497 A1 | 5/2008 | Wong et al. |
| 2008/0107787 A1 | 5/2008 | Prakash et al. |
| 2008/0292765 A1 | 11/2008 | Prakash et al. |
| 2008/0292775 A1 | 11/2008 | Prakash et al. |
| 2009/0017185 A1 | 1/2009 | Catani |
| 2009/0104330 A1 | 4/2009 | Zasypkin |
| 2009/0142817 A1 | 6/2009 | Norman et al. |
| 2009/0162499 A1 | 6/2009 | Mcardle et al. |
| 2010/0055752 A1 | 3/2010 | Kumar |
| 2011/0033525 A1 | 2/2011 | Liu |
| 2011/0111115 A1 | 5/2011 | Shi et al. |
| 2011/0124587 A1 | 5/2011 | Jackson et al. |
| 2011/0183056 A1 | 7/2011 | Morita et al. |
| 2011/0189360 A1 | 8/2011 | Yoo et al. |
| 2013/0347140 A1 | 12/2013 | Wang |
| 2015/0031868 A1 | 1/2015 | Lehmann et al. |

FOREIGN PATENT DOCUMENTS

| | | |
|---|---|---|
| CN | 1112565 | 11/1995 |
| CN | 1192447 | 9/1998 |
| CN | 1238341 | 5/2002 |
| CN | 1349997 A | 5/2002 |
| CN | 101200480 | 6/2008 |
| CN | 101591365 A | 12/2009 |
| CN | 101628924 | 1/2010 |
| EP | 0957178 | 2/2000 |
| EP | 2433505 | 3/2012 |
| EP | 2510800 | 10/2012 |
| JP | 52005800 | 1/1977 |
| JP | 52083731 | 7/1977 |
| JP | 52100500 | 8/1977 |
| JP | 52136200 | 11/1977 |
| JP | 54030199 | 3/1979 |
| JP | 54132599 | 10/1979 |
| JP | 55039731 | 3/1980 |
| JP | 55081567 | 6/1980 |
| JP | 55092400 | 7/1980 |
| JP | 55120770 | 9/1980 |
| JP | 55138372 | 10/1980 |
| JP | 55159770 | 12/1980 |
| JP | 55162953 | 12/1980 |
| JP | 56099768 | 8/1981 |
| JP | 56109568 | 8/1981 |
| JP | 56121453 | 9/1981 |
| JP | 56121454 | 9/1981 |
| JP | 56121455 | 9/1981 |
| JP | 56160962 | 12/1981 |
| JP | 57002656 | 1/1982 |
| JP | 57005663 | 1/1982 |
| JP | 57046998 | 3/1982 |
| JP | 57075992 | 5/1982 |
| JP | 57086264 | 5/1982 |
| JP | 58020170 | 2/1983 |
| JP | 58028246 | 2/1983 |
| JP | 58028247 | 2/1983 |
| JP | 58212759 | 12/1983 |
| JP | 58212760 | 12/1983 |
| JP | 59045848 | 3/1984 |
| JP | 59183670 | 10/1984 |
| JP | 60188035 | 9/1985 |
| JP | 62166861 | 7/1987 |
| JP | 63173531 A | 7/1988 |
| JP | 1131191 | 5/1989 |
| JP | 3262458 | 11/1991 |
| JP | 6007108 | 1/1994 |
| JP | 6192283 | 7/1994 |
| JP | 7143860 | 6/1995 |
| JP | 7177862 | 7/1995 |
| JP | 8000214 | 1/1996 |
| JP | 9107913 | 4/1997 |
| JP | 2000236842 | 9/2000 |
| JP | 2000270804 | 10/2000 |
| JP | 2002262822 | 9/2002 |
| JP | 2010516764 | 5/2010 |
| KR | 20070067199 | 6/2007 |
| KR | 20080071605 | 8/2008 |
| KR | 20090021386 | 3/2009 |
| RU | 2111969 | 5/1998 |
| RU | 2123267 | 12/1998 |
| RU | 2156083 | 9/2000 |
| RU | 2167544 | 5/2001 |
| RU | 2198548 | 2/2003 |
| WO | 2005089483 | 9/2005 |
| WO | 2006072878 | 7/2006 |
| WO | 2006072879 | 7/2006 |
| WO | 2007061795 | 5/2007 |

(56) References Cited

FOREIGN PATENT DOCUMENTS

| | | |
|---|---|---|
| WO | 2008091547 | 7/2008 |
| WO | 2008112966 | 9/2008 |
| WO | 2009071277 | 6/2009 |
| WO | 2009108680 | 9/2009 |
| WO | 2009140394 | 11/2009 |
| WO | 2010038911 | 4/2010 |
| WO | 2010118218 | 10/2010 |
| WO | 2010146463 | 12/2010 |
| WO | 2011046423 | 4/2011 |
| WO | 2011059954 | 5/2011 |
| WO | 2011097359 | 8/2011 |
| WO | 2011112892 | 9/2011 |
| WO | 2011153378 A1 | 12/2011 |
| WO | 2012006728 | 1/2012 |
| WO | 2012082493 | 6/2012 |
| WO | 2012082677 | 6/2012 |
| WO | 2012088593 | 7/2012 |
| WO | 2012102769 | 8/2012 |
| WO | 2012112180 | 8/2012 |
| WO | 2012125991 | 9/2012 |
| WO | 2012129451 | 9/2012 |
| WO | 2012166163 | 12/2012 |
| WO | 2012166164 | 12/2012 |
| WO | 2013022989 | 2/2013 |
| WO | 2013110673 | 8/2013 |
| WO | 2013176738 | 11/2013 |
| WO | 2014122227 | 8/2014 |
| WO | 2014122328 | 8/2014 |
| WO | 2014146089 | 9/2014 |
| WO | 2014146135 | 9/2014 |
| WO | 2014193888 | 12/2014 |

OTHER PUBLICATIONS

Liu, et al., "Study of stevioside preparation by membrane separation process", Desalination, vol. 83 1991, 375-382.
Lobov, S. V. et al., "Enzymic Production of Sweet Stevioside Derivatives: Transglucosylation of Glucosidases", Agric. Biol. Chern., vol. 55, No. 12 1991, 2959-2965.
Montovaneli, et al., "The effect of temperature and flow rate on the clarification of the aqueous Stevia-extract in fixed-bed col. with zeolites", Brazilian Journal of Chemical Engineering, vol. 21, No. 3 2004, 449-458.
Moraes, et al., "Clarification of Stevia rebaudiana (Bert.) Bertoni extract adsorption in modified zeolites", Acta Scientiarum, vol. 23, No. 6 2001, 1375-1380.
News Bites, GLG announces high purity Reb M Gras notification with FDA. Consumer Durables & Apparel Melbourne. Apr. 15, 2014. pp. 1-2. especially, p. 1, para 5; p. 2, para 1.
Ohio "14.0 Spray Drying and Spray Dryers", pp. 1-10, http://classfst.ohio-state-edu/Dairy.sub.-Tech/14Spraydrying.html Nov. 2, 2009 as obtained by internetarchive.org.
Ohta et al., "Characterization of Novel Steviol Glycosides from Leaves of Stevia rebaudiana Morita," J. AppL Glycosi., vol. 57, 199-209, 2010.
Ohtani et al. "Chapter 7. Methods to improve the taste of the sweet principles of Stevia rebaudiana." The Genus Stevia, edited by A. Douglas Kinghom, CRC Press 2001, Taylor and Francis, London and New York, pp. 138-159.
Philips, K.C. "Stevia: steps in developing a new sweetener", In T.H. Grenby, Editor, Developments in Sweeteners-3, Elsevier 1987, 1-43.
Pol, et al., "Comparison of two different solvents employed for pressurised fluid extraction of stevioside from Stevia Rebaudiana: methanol versus water", Anal Bioanal Chern vol. 388 2007, 1847-1857.
Pol, et al., "Characterisation of Stevia Rebaudiana by comprehensive two-dimensional liquid chromatography time-of-flight mass spectrometry," Journal of Chromatography A, 1150 (2007) 85-92.
Prakash et al., "Development of rebiana, a natural, non-caloric sweetener," Jul. 1, 2008, Food and Chemical Toxicology, vol. 46, Is. 7, Sup. 1, p. S75-S82.

Prakash et al. "Isolation and Characterization of a Novel Rebaudioside M Isomer from a Bioconversion Reaction of Rebaudioside A and NMR Comparison Studies of Rebaudioside M Isolated from Stevia rebaudiana Bertoni and Stevia Rebaudiana Morita," Biomolecules, vol. 4, 2014, 374-389, p. 385 para 5.
Prakash et al., "Development of Next Generation Stevia Sweetener: Rebaudioside M" Foods 2014, 3, 162-175, ISSN 2304-8158.
Rebaudioside A and Stevia Extract, Internet Citation, 2007 http://emperorsherbologist.com/rebaudioside.sub.-a.php. ?. 1-3.
Richman et al., "Fuctional genomics uncovers three glucosyltransferases involved in the synthesis of the major sweet glucosides of Stevia rebaudiana," The Plant Journal, vol. 41 (2005) 56-67.
Sakamoto et al., "Application of 13C NMR Spectroscopy to Chemistry of Natural Glycosides: Rebaudioside-C, a New Sweet Diterpene Glycoside of Stevia Rebaudiana", Chem Pharm. Bull., vol. 25, 1977, 844-846.
Shi, et al. "Synthesis of bifuntional polymeric adsorbent and its application in purification of Stevia glycosides", Reactive & functional Polymers, vol. 50 2002, 107-116.
Shibata et al. "Glucosylation of Steviol and Steviol-Glucosides in Extracts from Stevia rebaudiana Bertoni," Plant Physiol, vol. 95, (1991) 152-156.
Starratt, et al. "Rebaudioside F, a diterpene glycoside from Stevia Rebaudiana", Phytochemistry, vol. 59 2002, 367-370.
Sweet Green Fields, LLC "Notice to the U.S. Food and Drug Administration (FDA) that the use of Rebiana (Rebaudiosid A) derived from Stevia rebaudiana, as a Food Ingredient is Generally Recognized as Safe (GRAS)," Jan. 15, 2009, http:/www.accessdataida.gov/scripts/fcn/gras.sub.-notices/grn000282.pdf (obtained from the Web on May 8, 2012) entire document esp. p. 22, Table 1.
Tanaka, O., "Improvement of taste of natural sweeteners," Pure & Appl. Chem., vol. 69, No. 4 1997, 675-683.
Teo, et al. "Validation of green-solvent extraction combined with Chromatographic chemical fingerprint to evaluate quality of Stevia reaudiana Bertoni", J Sep. Sci, vol. 32 2009, 613-622.
Toyo sugar, "GRAS Exemption Claim for a-Glucosylated Steviol Glycosides" Office of Food Additive Safety. Feb. 23, 2011.
United Nations' Food and Agriculture Organization/Joint Expert Committee on Food Additives (2010) Steviol Glycosides, Compendium of Food Additive Specifications, FAO JECFA Monographs 10, 17-21.
Un "Steviol Glycosides" JECFA 2008 pp. 1-4, UN "Steviol Glycosides" JECFA 2008 pp. 1-4 http://www.fao.org/ag/ag/agn/jecfa-additives/specs/monograph5/additive-44-2-m5.pdf.
van der Maarel et al., "Properties and applications of starch-converting enzymes of the a-amylase family," Journal of Biotechnology, vol. 94 (220) 137-155.
Vasquez et al., Stimulation of the Gerbil's Gustatory Receptors by Some Potently Sweet Terpenoids, J. Agric. Food Chem., vol. 41, 1305-1310, 1993.
Wallin, "Steviol glycosides," 2004, XP002740430 ftp://ftp.fao.org/es/esn/jecfa/cta/CTA63.sub.-Steviol.pdf, pp. 1, 4, 5. Retrieved 2015.
Yamamoto, K. et al., "Effective Production of Glycosyl-steviosides by a-1, 6 Transglucosylation of Dextrin Dextranase", Biosci. Biotech. Biochem. vol 58, No. 9 1994, 1657-1661.
Ye, et al. "Modification of stevioside using transglucosylation activity of Bacilllus amyloliquefaciens a-amylase to reduce its bitter aftertaste," LWT-Food Science and Technology, vol. 51, Issue 1, May 2013, pp. 524-530.
Yoshikawa, et al. "Transglycosylation of Mogroside V, a Triterpene Glycoside in Siraitia grosvenori, by Cyclodextrin Glucanotransferase and Improvement of the Qualities of Sweetness," The Japanese Society of Applied Glycoscience, vol. 52, No. 3, 2005, p. 247-252.
Yoda, et al. "Supercritical fluid extraction from Stevia rebaudiana Bertoni using C02 and C02+ water: extraction kinetics and identification of extracted components", Journal of Food Engineering, vol. 57 2003, 125-134.
Remington: The Science and Practice of Pharmacy, 21st Edition. The University of the Sciences in Philadelphia, 2006. Part 5, p. 700.
"Toxicity, Alcohols". Available online as of Jan. 29, 2010 from emedicine.medscape.com. pp. 1-4.

(56) References Cited

OTHER PUBLICATIONS

Zell, et al. "Investigation of Polymorphism in Aspartame and Neotame Using Solid-State NMR Spectroscopy", Tetrahedron, vol. 56, 2000, 6603-6616.
"Methanol". Available online from Sigma-Aldrich as of Jan. 4, 2016. pp. 1-2.
"Acetone". Available online from Sigma-Aldrich as of Jan. 4, 2016. pp. 1-2.
Zhang, et al. "Membrane-based separation schemem for processing sweetener from Stevia leaves", Food Research International, vol. 33 2000, 617-620.
GRAS notification for Rebaudioside A (Jan. 19, 2009).
Stevia: The Journey from GRAS to Grocery (Webinar dated May 12, 2010).
PureVia website (http://www.purevia.com/nature/Stevia.aspx accessed online Jan. 13, 2016).
Ash et al (Handbook of Fillers, Excipients and Diluents, 2nd Ed, 2007—p. 187).
Ohwoavworhua et al (Indian J Pharm Sci 72:295-301, 2010).
GRAS Assessment of Rebaudioside A (dated Jan. 19, 2009).
Oluwasina et al (BioResources 9:6166-6192, 2014) (Year: 2014).
Altrista et al (J Young Pharm 10(Suppl S2):s79-s83, 2018 (Year: 2018).
Kinghorn, "Overview", Stevia: The genus Stevia, Taylor & Francis, 2002, 1-17.
Derwent Summary, Derwent Acc No. 2007-417163 (including summary of Jeong (KR 2006/109581).
Oram ("The pH of Water" available online at http://www.water-research.net/index.php/ph, accessed Oct. 14, 2016).
A-Glucosyltransferase Treated Stevia, Japan's Specifications and Standards for Food Additives, VIII edition, 2009, p. 257.
Ahmed, et al., "Use of p-Bromophenacyl Bromide to Enhance Ultraviolet Detection of Water-Soluble Organic Acids (Steviolbioside and Rebaudioside B) in High-Performance Liquid Chromatographic Analysis", Journal of Chromatography, vol. 192, 1980, 387-393.
Chang, S. S. et al., "Stability Studies of Stevioside and Rebaudioside A in Carbonated Beverages", Journal of Agricultural and Food Chemistry, vol. 31, 1983, 409-412.
Chen, et al., "Enrichment and separation of rebaudioside A from stevia glycosides by a novel adsorbent with pyridyl group", Science in China, vol. 42, No. 3 1999, 277-282.
Chen, et al., "Selectivity of polymer adsorbent in adsorptive separations of stevia diterpene glycisides", Science in China, vol. 41, No. 4 1998, 436-441.
Chen, et al., "Studies on the adsorptive selectivity of the polar resin with carbonyl group on rebaudioside A", Acta Polymeric Scnica, No. 4 1999, 398-403.
Crammer, et al., "Sweet glycosides from the Stevia plant", Chemistry in Britain, Oct. 1986, 915-916, 918.
Chatsudthipong, et al. Stevioside and related compounds: Therapeutic benefits beyond sweetness, pp. 41-45 Pharmacology & Therapeutics 121 (2009).
Darise et al., "Enzymic Transglucosylation of Rubusoside and the Structure-Sweetness Relationship of Steviol Bisglycosides," Agric. Biol. Chem, vol. 48(10), 1984, 2483-2488.
Dubois et al., "Diterpenoid Sweeteners. Synthesis and Sensory Evaluation of Stevioside Analogues with Improved Organoleptic Properties," J. Med Chem, vol. 28, (1985) 93-98.
FAO/WHO "Combined Compendium of Food Additive Specifications" FAO JECFA Monographs 1, vol. 4, 2006, Food and Agricultural Organization of the United Nations, Rome.
Fuh, "Purification of steviosides by membrane and ion exchange process", Journal of Food Science, vol. 55, No. 5 1990, 1454-1457.
Fukunaga et al., "Enzymic Transglucosylation Products of Stevioside: Separation and Sweetness-evaluation," Agric. Biol. Chem, vol. 53(6) (1989) 1603-1607.
Fullas et al., "Separation of natural product sweetening agents using overpressured layer chromatography," Journal of Chromatography vol. 464 (1989) 213-219.
Hale, et al., "Amylase of Bacillus Macerans", Cereal Chemistry, vol. 28, No. 1, Jan. 1951, 49-58.
International Search Report and Written Opinion of PCT/US2010/055960.
International Search Report and Written Opinion of PCT/US2011/028028.
International Search Report and Written Opinion of PCT/US2011/033734.
International Search Report and Written Opinion of PCT/US2011/033737.
International Search Report and Written Opinion of PCT/US2011/033912.
International Search Report and Written Opinion of PCT/US2011/035173.
International Search Report and Written Opinion of PCT/US2011/036063.
International Search Report and Written Opinion of PCT/US2011/047498.
International Search Report and Written Opinion of PCT/US2011/047499.
International Search Report and Written Opinion of PCT/US2011/064343.
International Search Report and Written Opinion of PCT/US2012/024585.
International Search Report and Written Opinion of PCT/US2012/024722.
International Search Report and Written Opinion of PCT/US2012/030210.
International Search Report and Written Opinion of PCT/US2012/043294.
International Search Report and Written Opinion of PCT/US2012/051163.
International Search Report and Written Opinion of PCT/US2012/052659.
International Search Report and Written Opinion of PCT/US2012/052665.
International Search Report and Written Opinion of PCT/US2013/030439.
International Search Report and Written Opinion of PCT/US2015/047234.
Kobayashi, et al., "Dulcoside A and B, New diterpene glycosides from Stevia Rebaudiana", Phytochemistry, vol. 16 1977, 1405-1408.
Kitahata, S. et al., "Production of Rubusoside Derivatives by Transgalactosylation of Various b-Galactosidases" Agric. Biol. Chem., vol. 53, No. 11 1989, 2923-2928.
Gorden et al. ("Supersaturation" Access Science McGraw Hill 2008, p. 1, http://www.accessscience.com/content/supersaturation/670000).
Hartel, Richard "Crystallization in Foods" Handbook of Industrial Crystallization Elsevier 2002, pp. 287 and 293-296.
"Recrystallization Technique: Proper purification of crystalline solids". Available online as of Dec. 4, 2009 from www.growid.org. pp. 1-3.
Huang, X Y, et al. "Preparative isolation and purification of steviol glycosides from Stevia rebaudiana Bertoni using high-speed counter-current chromatogoraphy" Separation and Purification Technology Elsevier Science, Netherlands, vol. 71, No. 2, 2010, p. 220-224.
Jaitak, et al., "An Efficient Microwave-assisted Extraction Process of Stevioside and Rebaudioside-A from Stevia Rebaudiana (Bertoni)", Phytochem. Anal vol. 20 2009, 240-245.
Kennelly, "Sweet and non-sweet constituents of Stevia rebaudiana", Stevia: The genus Stevia, Taylor & Francis, 2002, 68-85.

* cited by examiner

PRODUCTS FROM STEVIA RABAUDIANA

RELATED APPLICATIONS

This application claims the benefit of U.S. Provisional Application No. 62/172,525, filed Jun. 8, 2015, and this application is a continuation-in-part application of: U.S. patent application Ser. No. 14/195,812 entitled "Products From Stevia Rebaudiana", filed Mar. 3, 2014; U.S. patent application Ser. No. 13/943,776 entitled "Food Ingredients From Stevia Rebaudiana", filed Jul. 16, 2013; which claims the benefit U.S. patent application Ser. No. 13/530,113 filed Jun. 22, 2012 (now U.S. Pat. No. 8,530,527); which claims the benefit under 35 U.S.C. 119(e) of U.S. Provisional Application No. 61/500,598 entitled "Food Ingredients From Stevia Rebaudiana", filed Jun. 23, 2011; each of which are herein incorporated by reference in their entireties.

FIELD OF THE INVENTION

The invention relates to a process for producing food ingredients and other products from Stevia rebaudiana plant biomass and their use in various applications including food products and beverages.

BACKGROUND OF THE INVENTION

Nowadays sugar alternatives are receiving increasing attention due to awareness of many diseases in conjunction with consumption of high-sugar foods and beverages. However many artificial sweeteners such as dulcin, sodium cyclamate and saccharin were banned or restricted in some countries due to concerns on their safety. Therefore non-caloric sweeteners of natural origin are becoming increasingly popular. The sweet herb Stevia rebaudiana Bertoni produces a number of diterpene glycosides which feature high intensity sweetness and sensory properties superior to that of many other high potency sweeteners.

The above-mentioned sweet glycosides have a common aglycon, steviol, and differ by the number and type of carbohydrate residues at the C13 and C19 positions. The leaves of Stevia are able to accumulate up to 10-20% (on dry weight basis) steviol glycosides. The major glycosides found in Stevia leaves are rebaudioside A (2-10%), stevioside (2-10%), and rebaudioside C (1-2%). Other glycosides such as rebaudioside B, D, E, and F, steviolbioside and rubusoside are found at much lower levels (approx. 0-0.2%).

Methods for the extraction and purification of sweet glycosides from the Stevia rebaudiana plant using water or organic solvents are described in, for example, U.S. Pat. Nos. 4,361,697; 4,082,858; 4,892,938; 5,972,120; 5,962,678; 7,838,044 and 7,862,845.

As it is well known the use of high intensity sweeteners in various applications requires various bulking agents to substitute the sugar which is removed from the formulation. The bulking agents used in those applications include both caloric and non-caloric materials. Non limiting examples of bulking agents include fructooligosaccharides, inulin, inulooligosaccharides, maltooligosaccharides, maltodextins, cyclodextrins, corn syrup solids, erythritol and other sugar alcohols, glucose, maltose, lactose, tagatose, lactulose, palatinose, isomalt, modified starches etc.

Obviously more preferable are the bulking agents which provide zero calories, such as erythritol, isomalt, fructooloigosacharides, inulin etc.

On the other hand it has to be noted that steviol glycosides are compounds extracted from the plant and in process of their manufacture large amounts of "empty" biomass is created. Moreover, generally, the extraction process utilizes only the Stevia plant leaves. This additionally generates large amount of the stems which have limited use as well. The "empty" biomass is mainly discharged directly to environment. In some cases it is used for biogas production. It might be used as biofertilizer as well. The stems are generally used as fuel.

There is no reports to-date on processing the stevia biomass into any food ingredient. Nevertheless, if accomplished in large scale, this can provide significant economic, and environmental benefits as it can provide an opportunity for inclusion of whole stevia plant into food chain, creating practically wasteless stevia processing.

Within the description of this invention we will show that, stevia plant biomass may be used as a source for producing valuable food ingredients and other chemicals, which can be used in number of areas including food and beverage applications.

SUMMARY OF THE INVENTION

The present invention is aimed to overcome the disadvantages of existing Stevia industrial processing schemes. The invention describes a process for producing high value products and food ingredients from the Stevia rebaudiana plant biomass and use thereof in various food products and beverages as a carrier or bulking agent.

The invention, in part, pertains to high value products comprising cellulose, or cellulose containing biomass derived from Stevia rebaudiana Bertoni plant.

In the invention, Stevia rebaudiana Bertoni plant biomass, particularly the leaves and/or stems, were used as a starting material.

The starting material was subjected to size reduction, by means of rotary blade milling machine. The grinded biomass was subjected to water-soaking and alkaline pulping to obtain a pulp comprising of high content of cellulose, where the pulp can be used to produce for example glucose for further applications.

The pulp and/or any derivative thereof can be used as a feedstock for microorganism(s) for de novo biosynthesis of steviol glycosides molecules. Such steviol glycoside molecules can be considered as "stevia-derived", in contrast to current biosynthetic technology which synthesizes steviol glycoside molecules by recombinant microorganisms using non-stevia feedstock (e.g. cane sugar, corn starch, etc).

In addition, the pulp can be further processed by bleaching and acid hydrolysis and spray drying to produce a microcrystalline cellulose complying to specifications prepared at the 55th JECFA (2000) and published in FNP52 Add 8 (2000), where the microcrystalline cellulose can be used to produce for example glucose for further applications.

The obtained products are applicable to various foods and beverages as bulking agent, including tabletop sweeteners, soft drinks, ice cream, cookies, bread, fruit juices, milk products, baked goods and confectionary products.

Preferably the product of invention is used with other sweeteners, flavors and food ingredients.

Non-limiting examples of sweeteners include steviol glycosides, stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, rebaudioside P, rebaudioside Q, rebaudioside R, rebaudioside Z, dulcoside A, steviolbioside, rubusoside, as well as other steviol glycosides found in *Stevia rebaudiana* plant and mixtures thereof, stevia extract, Luo Han Guo extract, mogrosides, high-fructose corn syrup, corn syrup, invert sugar, fructooligosaccharides, inulin, allulose, tagatose, inulooligosaccharides, coupling sugar, maltooligosaccharides, maltodextrins, corn syrup solids, glucose, maltose, sucrose, lactose, aspartame, saccharin, sucralose, sugar alcohols.

The obtained products are also used as starting material for preparation of glucose, dextrose, ethyl alcohol, various polymers and other organic compounds.

It is to be understood that both the foregoing general description and the following detailed description are exemplary and explanatory and are intended to provide further explanation of the invention as claimed.

DETAILED DESCRIPTION OF THE INVENTION

Advantages of the present invention will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the invention, *Stevia rebaudiana* plant biomass, particularly the leaves and stems of *Stevia rebaudiana* plant, were used as a starting material. Other parts of *Stevia rebaudiana* plant can be used as well. The "empty" leaf biomass obtained after extraction of steviol glycosides, as well as *Stevia rebaudiana* plant stems remaining after "stripping-off" the leaves can be used as a starting material. The stevia biomass suitable for the process of the present invention includes processed *Stevia rebaudiana* plants (e.g., post-extraction of steviol glycosides) and parts thereof as well as un-processed *Stevia rebaudiana* plants and parts thereof.

The testing of obtained microcrystalline cellulose was conducted according to procedures set in microcrystalline cellulose monograph prepared at the 55th FAO/JECFA meeting (2000) and published in Food and Nutrition Paper 52 Addendum 8(2000).

The testing of obtained powder cellulose was conducted according to procedures set in powder cellulose monograph prepared at the 20th JECFA (1976), published in FNS 1B (1977) and in FNP 52 (1992).

In one embodiment of the invention, the starting material is milled using rotary blade grinder to produce particles from 1-50 mm, preferably 5-20 mm in length. Any other equipment capable of reducing large particles into smaller ones can be used in this stage as well.

In one embodiment of the invention the obtained grinded biomass is dispersed in the water and boiled at 100° C. for 0.5-3 hours, preferably 1-1.5 hours, followed by separation of the liquid and the water-insoluble stevia biomass. The process is repeated several times until colorless or substantially colorless liquid is obtained. A continuous extracting apparatus, as well as any other equipment known to those skilled in art, may be used for this purpose.

In one embodiment of this invention the separated stevia biomass is subsequently introduced into 10-20% NaOH aqueous solution. The solution is treated in pressurized vessel at 110-180° C., preferably 120-170° C., during 0.1-10 hours, preferably 1-5 hrs to produce pulped biomass. Other alkaline solutions can be used as well for this pulping step. Alternatively other pulping techniques such as biological or organic solvent pulping, mechanical, thermomechanical, chemo-thermomechanical, chemical pulping such as Kraft process, sulfite process can be used. After thermal treatment the pulped biomass is separated from the liquid and washed with water till neutral pH of washing water is achieved.

In one embodiment of this invention the washed biomass is optionally treated with bleaching agent. Various bleaching agents such as hydrogen peroxide, ozone, chlorine, sodium hypochlorite, chlorine oxide, enzymes may be used. However it is preferred to use chlorine-free bleaching agents.

In one embodiment of present invention the bleaching of pulped biomass is achieved by using 10-30%, preferably 20-25%, hydrogen peroxide. The biomass was suspended in 0.5-5, preferably 1-3 volumes of hydrogen peroxide and incubated at 80-150° C., preferably 100-120° C., during 0.1-3 hours, preferably 0.5-1.5 hours. The bleached biomass was subsequently separated from liquid and washed with water.

In one embodiment of this invention, the obtained biomass was subjected to partial depolymerization. Mechanical depolymerization (disintegration) and/or various agents capable of depolyimerizing the cellulose, such as mineral acids and enzymes, can be utilized for this stage.

In one embodiment of this invention the depolymerization is achieved by 1-20%, preferably 5-15% hydrochloric acid. The ratio of bleached biomass to acid solution is 1:0.5 to 1:5, preferably 1:1 to 1:3. The temperature of depolymerization process is 50-120° C., preferably 80-100° C. during 0.1-5 hours, preferably 0.5-2 hours.

In one embodiment the obtained depolymerized cellulose is separated from acid solution and washed with water until neutral pH is achieved. The obtained solids are suspended in 1-3 volumes of water and spray dried at inlet temperature of 180° C. and outlet temperature of 100° C.

In one embodiment of this invention the cellulose is mechanically disintegrated to produce powder cellulose (INS 460ii).

In one embodiment of present invention a stevia sweetener is added to depolymerized cellulose slurry. The ratio of stevia sweetener to depolymerized cellulose on dry weight basis is 1:50 to 1:400 (wt), preferably 1:100 to 1:300.

Any other drying techniques such as flash drying, or vacuum drying can be used for the drying of the slurry as well.

Non-limiting examples of stevia sweeteners include stevia extract, steviol glycosides, stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, rebaudioside P, rebaudioside Q, rebaudioside R, rebaudioside Z, dulcoside A, steviolbioside, rubusoside, as well as other steviol glycosides found in *Stevia rebaudiana* plant and mixtures thereof.

Alternatively the cellulose produced by the method of this invention can be processed into other food ingredients by techniques known to those skilled in art. Non-limiting examples of such ingredients include, water soluble cellulose, carboxymethyl cellulose, methylcellulose, hydroxypropylcellulose, hydroxypropyl-methylcellulose, ethylmethylcellulose as well as cellobiose, glucose etc.

Alternatively the cellulose containing materials produced by the method of this invention can be processed into other chemicals and products by techniques known to those skilled in art. Non limiting examples of such techniques include, mechanical processing (crushing, milling, grinding, pressing, drying, disintegrating, etc), chemical/enzymatic hydrolysis, biotransformation, fermentation (including fermentation by recombinant microorganisms or genetically modified microbial host cells), chemical synthesis, biocatalysis, chemical catalysis, bioconversion, biodegradation, derivatization, polymerization, chemical/enzymatic isomerization, etc. Non limiting examples of organic chemicals include, monosaccharides, oligosaccharides, polysaccharides, alcohols, polyols, organic acids, carboxylic acids and salts thereof, biofuels, biodegradable polymers, recyclable polymers, food grade polymers, packaging materials, inks, various grades of paper, ethanol, PET, polyethylene terephthalate, monoethylene glycol, MEG, ethylene glycol, ethylene, terephthalic acid, lactic acid, etc.

In one particular embodiment the cellulose containing materials produced by the method of this invention are useful as stevia-derived feedstock, including but not limited to pulp, bleached pulp, purified cellulose, hydrolyzed cellulose, depolymerized cellulose, disintegrated cellulose, dextrose, which is contacted with recombinant microorganism(s) to produce steviol glycosides. Non limiting examples of steviol glycosides include stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, rebaudioside P, rebaudioside Q, rebaudioside R, rebaudioside Z, dulcoside A, steviolbioside, rubusoside, alpha-glucosylated steviol glycosides, as well as other steviol glycosides found in *Stevia rebaudiana* plant and mixtures thereof.

The products of present invention can be used as bulking agents, sweeteners, flavor enhancers in various food and beverage products. Non-limiting examples of food and beverage products include tabletop sweeteners, carbonated soft drinks, flavored carbonated soft drinks, cola flavored carbonated soft drinks, lemon lime flavored carbonated soft drinks, low-calorie carbonated soft drinks, zero-calorie carbonated soft drinks, ready to drink beverages, energy drinks, isotonic drinks, low-calorie drinks, zero-calorie drinks, sports drinks, teas, fruit and vegetable juices, juice drinks, dairy drinks, yoghurt drinks, alcohol beverages, powdered beverages, bakery products, cookies, biscuits, baking mixes, cereals, confectioneries, candies, toffees, chewing gum, dairy products, flavored milk, yoghurts, flavored yoghurts, cultured milk, soy sauce and other soy base products, salad dressings, mayonnaise, vinegar, frozen-desserts, meat products, fish-meat products, bottled and canned foods, fruits and vegetables.

Additionally the products can be used in drug or pharmaceutical preparations and cosmetics, including but not limited to toothpaste, mouthwash, cough syrup, chewable tablets, lozenges, vitamin preparations, and the like.

The products can be used "as-is" or in combination with other sweeteners, flavors and food and beverage ingredients.

Non-limiting examples of sweeteners include steviol glycosides, stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, rebaudioside P, rebaudioside Q, rebaudioside R, rebaudioside Z, dulcoside A, steviolbioside, rubusoside, as well as other steviol glycosides found in *Stevia rebaudiana* plant and mixtures thereof, stevia extract, Luo Han Guo extract, mogrosides, high-fructose corn syrup, corn syrup, invert sugar, fructooligosaccharides, inulin, inulooligosaccharides, coupling sugar, maltooligosaccharides, maltodextrins, corn syrup solids, glucose, maltose, sucrose, allulose, tagatose, lactose, aspartame, saccharin, sucralose, sugar alcohols.

Non-limiting examples of flavors include lemon, orange, fruit, banana, grape, pear, pineapple, bitter almond, cola, cinnamon, sugar, cotton candy, vanilla flavors.

Non-limiting examples of other food ingredients include flavors, acidulants, organic and amino acids, coloring agents, bulking agents, modified starches, gums, texturizers, preservatives, antioxidants, emulsifiers, stabilisers, thickeners, gelling agents, caffeine.

The following examples illustrate various embodiments of the invention. It will be understood that the invention is not limited to the materials, proportions, conditions and procedures set forth in the examples, which are only illustrative.

Example 1

Preparation of Stevia Ingredient 1 kg of *Stevia rebaudiana* plant dried leaves were grinded into pieces of approx 10 mm, suspended in 5 L of water and boiled for 1 hour. The liquid was removed and the separated biomass was resuspended in the water and treated as described above. The process was repeated 5 times. The resulted biomass was suspended in 3 L 15% NaOH solution and placed into autoclave for pulping at 150° C. for 2 hrs. The obtained pulped biomass is separated from liquid and washed with deionized water till neutral pH of washing water. The washed pulp was suspended in 3 L of 20% hydrogen peroxide and treated for 1 hr at 100° C. The bleached pulp was washed with water and suspended in 3 L 10% hydrochloric acid. The mixture was heated to 90° C. for 1 hr. The obtained mixture was strained through 60 mesh sieve and then filtered through grade 1 filter paper. The solids recovered on the filter paper were washed with deionozed water till neutral pH of washing water was achieved. The washed were suspended in 1.5 L of water and spray dried by YC-015 laboratory spray drier (Shanghai Pilotech Instrument & Equipment Co. Ltd., China) operating at 180° C. inlet and 100° C. outlet temperature. About 480 g of free flowing microcrystalline cellulose was obtained.

Example 2

Preparation of Stevia Ingredient 1 kg of *Stevia rebaudiana* plant dried stems were processed similarly to leaves according to EXAMPLE 1. About 670 g of free flowing microcrystalline cellulose was obtained.

Example 3

Preparation of Stevia Composition

About 500 g of microcrystalline cellulose prepared according to example 1 or 2 was added to 1500 mL water solution containing 2.5 g of rebaudioside A produced by PureCircle Sdn. Bhd. (Malaysia) with purity of 99.5% (dry basis). The mixture was spray dried to yield about 490 g of dry powder.

Example 4

Preparation of Pulp from Stevia Plant 1 kg of *Stevia rebaudiana* plant dried stems were grinded into pieces of approx 10 mm, suspended in 5 L of water and boiled for 1 hour. The liquid was removed and the retained biomass was suspended in 6 L 20% NaOH solution and placed into digester for pulping at 170° C. for 2 hrs. The obtained pulped biomass is separated from liquid and washed with deionized water. The washed pulp was reduced in a homogenizer to yield 400 g of unbleached pulp. The analysis results show 99.2% carbohydrate calculated as cellulose on dry basis, and 0.08% sulfated ash content (Microcrystalline Cellulose, FAO Food and Nutrition Paper 52 Addendum 8(2000)).

Example 5

Preparation of Glucose from Pulp 10 g of unbleached pulp prepared according to EXAMPLE 4 was suspended in 500 mL of 5% $H_2SO_4$ solution and incubated at 100° C. for 2 hours. The reaction was stopped by neutralizing the reaction mixture with 20% NaOH. The obtained solution was passed through columns packed with Amberlite FPC23H and Amberlite FPA51 ion exchange resins and the glucose concentration was determined by Somogyi-Nelson reducing sugar method (Somogyi, M. (1952). J. Biol. Chem., 200, 245). The yield of glucose was 52%.

Example 6

Preparation of Glucose from Pulp 10 g of unbleached pulp prepared according to EXAMPLE 4 was mixed with 100 mL 0.5% $H_2SO_4$ and incubated at 100° C. for 20 min. Then the pulp was washed with water until neutral pH. The washed pulp was mixed with 200 mL of water, 250 FPU of "Cellulase GC 220®" (Genencor, USA), 750 IU of "Novozyme 188®" β-glucosidase (Novozymes, Denmark), and the reaction was conducted at pH 5.0 and 50° C. for 48 hrs. The reaction was stopped by boiling for 10 min at 100° C. The glucose concentration was determined by Somogyi-Nelson reducing sugar method (Somogyi, M. (1952). J. Biol. Chem., 200, 245). The yield of glucose was 82%.

Example 7

Fermentation of Glucose to Ethanol

10 L of glucose solution prepared according to EXAMPLE 6 was concentrated to 10% solids content and fermented with *Saccharomyces cerevisiae* St-50 (Culture Collection of PureCircle Sdn. Bhd., Malaysia) at 28° C. during 24 hrs. The Ethanol from fermented solution was recovered by distillation to obtain 260 mL of 95% (v/v) Ethanol.

It is to be understood that the foregoing descriptions and specific embodiments shown herein are merely illustrative of the best mode of the invention and the principles thereof, and that modifications and additions may be easily made by those skilled in the art without departing for the spirit and scope of the invention, which is therefore understood to be limited only by the scope of the appended claims.

I claim:

1. A process for producing a stevia food ingredient, comprising the steps of
   (a) providing a stevia biomass from *Stevia rebaudiana* plant;
   (b) incubating soaking the water insoluble stevia biomass in water to remove water soluble components and then separating them into water-insoluble stevia biomass and water-based filtrate;
   (c) incubating the water-insoluble stevia biomass from step (b) in an alkaline solution to produce a pulp;
   (d) processing the pulp from step (c) to produce one or more material selected from the group consisting of: bleached pulp, purified cellulose, hydrolyzed cellulose, depolymerized cellulose, disintegrated cellulose, dextrose, and combinations thereof; and
   (e) contacting the material from step (d) with a recombinant microorganism to produce a stevia food ingredient,
   wherein the stevia food ingredient is selected from the group consisting of: stevioside, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, rebaudioside P, rebaudioside Q, rebaudioside R, rebaudioside Z, dulcoside A, steviolbioside, rubusoside, alpha-glucosylated steviol glycosides, other steviol glycosides found in *Stevia rebaudiana* plant, and combinations thereof.

2. The process of claim 1, further comprising the step of combining the stevia ingredient with a food, beverage, drug, pharmaceutical, cosmetic or consumable product.

3. The process of claim 1, further comprising the step of combining the stevia ingredient with a stevia-derived cellulose.

4. The process of claim 3, wherein the stevia-derived cellulose is obtained from a second water-insoluble stevia biomass.

5. The process of claim 4, wherein the second water-insoluble stevia biomass is treated with an alkaline solution and bleached to form the stevia-derived cellulose.

* * * * *